(12) United States Patent
Crabb et al.

(10) Patent No.: US 8,137,991 B2
(45) Date of Patent: Mar. 20, 2012

(54) METHODS OF REDUCING ANGIOGENESIS OF AGE-RELATED MACULAR DEGENERATION (AMD) OR CHOROIDAL NEOVASCULARIZATION BY AN ANTI-CARBOXYETHEYLPYRROLE (CFP) ANTIBODY

(75) Inventors: John W. Crabb, Chagrin Falls, OH (US); Robert G. Salomon, Mayfield Village, OH (US); Bela Anand-Apte, Shaker Heights, OH (US); Quteba Ebrahem, Shaker Heights, OH (US); Kutralanathan Reganathan, Cleveland, OH (US)

(73) Assignees: The Cleveland Clinic Foundation, Cleveland, OH (US); Case Western Reserve University, Cleveland, OH (US)

( * ) Notice: Subject to any disclaimer, the term of this patent is extended or adjusted under 35 U.S.C. 154(b) by 160 days.

(21) Appl. No.: 12/374,747

(22) PCT Filed: Jul. 23, 2007

(86) PCT No.: PCT/US2007/016619
§ 371 (c)(1),
(2), (4) Date: Jan. 22, 2009

(87) PCT Pub. No.: WO2008/013797
PCT Pub. Date: Jan. 31, 2008

(65) Prior Publication Data
US 2010/0143380 A1    Jun. 10, 2010

Related U.S. Application Data

(60) Provisional application No. 60/832,898, filed on Jul. 24, 2006.

(51) Int. Cl.
*G01N 33/53* (2006.01)
*A61K 39/395* (2006.01)
*A61K 39/00* (2006.01)
*C70K 14/515* (2006.01)

(52) U.S. Cl. ..... 436/547; 436/548; 436/543; 424/130.1; 424/141.1; 424/142.1; 514/13.3

(58) Field of Classification Search .......................... None
See application file for complete search history.

(56) References Cited

U.S. PATENT DOCUMENTS

| | | |
|---|---|---|
| 7,172,874 B2 | 2/2007 | Hollyfield et al. |
| 2004/0265924 A1 | 12/2004 | Hollyfield et al. |
| 2009/0155243 A1 | 6/2009 | Perez et al. |

FOREIGN PATENT DOCUMENTS

| | | |
|---|---|---|
| WO | WO 2005/110114 A1 | 11/2005 |
| WO | WO 2007/127151 A2 | 11/2007 |
| WO | WO 2008/013797 A2 | 1/2008 |

OTHER PUBLICATIONS

Burgess et al. J of Cell Bio. 1990, 111:2129-2138.*
Pawson et al. 2003, Science 300:445-452.*
Haddad et al., Sury Ophthalmol. Jul.-Aug. 2006; 51:316-63.*
Jha et al., Mol. Immunol. Sep. 2007; 44: 3901-8.*
AREDS Research Group, "A Randomized, Placebo-Controlled, Clinical Trial of High-Dose Supplementation with Vitamins C and E, Beta Carotene, and Zinc for Age-Related Macular Degeneration and Vision Loss," *Arch. Ophthalmol.*, 119:1417-1436 (2001).
AREDS Research Group, "Laser Photocoagulation of Subfoveal Recurrent Neovascular Lesions in Age-Related Macular Degeneration," *Arch Ophthalmol.*, 109: 1232-1241. (1991).
AREDS Research Group, "Subfoveal Neovascular Lesions in Age-Related Macular Degeneration," *Arch. Ophthalmol.*, 109:1242-1257 (1991).
Beatty, S., et al., "The Role of Oxidative Stress in the Pathogenesis of Age-Related Macular Degeneration," *Survey of Ophthalmology*, 45(2):115-134 (2000).
Bok, D., "Evidence for an Inflammatory Process in Age-Related Macular Degeneration Gains New Supports," *PNAS*, 102(20):7053-7054 (2005).
Campochiaro, P.A., "Retinal and Choroidal Neovascularization," *Journal of Cellular Physiology*, 184:301-310 (2000).
Crabb, J.W., et al., "Drusen Proteome Analysis: An Approach to the Etiology of Age-Related Macular Degeneration," PNAS, 99(23):14682-14687 (2002).
Ebrahem, Q., et al., "Carboxyethylpyrrole Oxidative Protein Modifications Stimulate Neovascularization: Implications for Age-Related Macular Degeneration," PNAS, 103(36):13480-13484 (2006).
Edwards, A.O., et al., "Complement Factor H Polymorphism and Age-Related Macular Degeneration," *Science*. 308:421-424 (2005).
Fliesler, S.J. and Anderson, R.E., "Chemistry and Metabolism of Lipids in the Vertebrate Retina," *Prog Lipid Res.*, 22:2279-131 (1983).
Gu, X., et al., "Carboxyethlpyrrole Protein Adducts and Autoantibodies, Biomarkers for Age-Related Macular Degeneration," *The Journal of Biological Chemistry*, 278(43):42027-42035 (2003).

(Continued)

*Primary Examiner* — Chang-Yu Wang
(74) *Attorney, Agent, or Firm* — Hamilton, Brook, Smith & Reynolds, P.C.

(57) ABSTRACT

The present invention pertains to methods of inhibiting angiogenesis in an individual in need thereof comprising administering to the individual an agent that inhibits one or more CEP protein adducts wherein the angiogenesis is the result of oxidative peptide modification of polyunsaturated fatty acids (PUFA) in the individual, and administration of the agent inhibits angiogenesis in the individual. In one embodiment, the invention is directed to methods of inhibiting ocular angiogenesis in an individual in need thereof comprising administering to the individual an agent that inhibits the angiogenic activity of one or more CEP protein adducts wherein administration of the. agent inhibits ocular angiogenesis in the individual. In another embodiment, the invention is directed to methods of inhibiting choroidal neovascularization in an individual in need thereof comprising administering to the individual an agent that inhibits the angiogenic activity of one or more CEP protein adducts wherein administration of the agent inhibits choroidal neovascularization in the individual.

17 Claims, 6 Drawing Sheets

OTHER PUBLICATIONS

Gu, X., et al., "Oxidatively Truncated Docosahexaenoate Phospholipids: Total Synthesis, Generation, and Peptide Adduction Chemistry," *J. Org Chem.*, 68:3749-3761 (2003).

Hageman, G.S., et al., "A Common Haplotype in the Complement Regulatory Gene Factor H (HF1/CFH) Predisposes Individuals to Age-Related Macular Degeneration," *PNAS.* 102(20):7227-7232 (2005).

Haines, J.L., et al., "Complement Factor H Variant Increases the Risk of Age-Related Macular Degeneration," *Science*, 308:419-421 (2005).

Handa, J.T., et al., Increase in the Advanced Glycation End Product Pentosidine in Bruch's Membrane with Age, *IOVS*, 40(3):775-779 (1999).

Hirata, C., et al., "Advanced Glycation End Products Induce Expression of Vascular Endothelial Growth Factor by Retinal Müller Cells," *Biochemical and Biophysical Research Communications.*, 236:712-715 (1997).

Hoffmann, S., et al., "Advanced Glycation End Products Induce Choroidal Endothelial Cell Proliferations, Matrix Metalloproteinase-2 and VEGF Upregulation In Vitro," *Graefe's Arch. Clin. Exp. Ophthalmol.*, 240:996-1002 (2002).

Hoffmann, S., et al., "Selective Killing of RPE with a Vascular Endothelial Growth Factor Chimeric Toxin," *IOVS*, 41(8):2389-2393 (2000).

Ishibashi, T., et al., "Advanced Glycation End Products in Age-Related Macular Degeneration," *Arch. Ophthalmol.*, 116:1629-1632 (1998).

Kaur, K., et al., "(Carboxyalkyl)pyrroles in Human Plasma and Oxidized Low-Density Lipoproteins," *Chem. Res. Toxicol.*, 10:1387-1396 (1997).

Klein, R.J., et al., "Complement Factor H Polymorphism in Age-Related Macular Degeneration," *Science*, 308:385-389 (2005).

Malek, G., et al., "Apolipoprotin E Allele-Dependent Pathogenesis: A Model for Age-Related Retinal Degeneration," *Proc. Natl. Acad. Sci, USA*, 102(33):11900-11905 (2005).

Nguyen, M., et al., "Quantitation of Angiogenesis and Antiangiogenesis in the Chick Embryo Chorioallantoic Membrane," *Microvascular Research*, 47;31-40 (1994).

Okamoto, T., et al, Advanced Glycation End Products Induce Angiogenesis In Vivo, *Microvascular Research*, 63:186-195 (2002).

Podrez, E.A., et al., "A Novel Family of Atherogenic Oxidized Phospholipids Promotes Macrophage Foam Cell Formation Via the Scavenger Receptor CD36 and Is Enriched in Atherosclerotic Lesions," *The Journal of Biological Chemistry*, 277(41):38517-38523 (2002).

Podrez, E.A., et al., "Identification of a Novel Family of Oxidized Phospholipids that Serve as Ligands for the Macrophage Scavenger Receptor CD36*," *The Journal of Biological Chemistry*, 277(41):38503-38516 (2002).

Seddon, J.M., et al., "A Prospective Study of Cigarette Smoking and Age-Related Macular Degeneration in Women," *JAMA*, 276(14):1141-1146 (1996).

Subbanagounder, G., et al., "Hydroxy Alkenal Phospholipids Regulate Inflammatory Functions of Endothelial Cells," *Vascular Pharmacology*, 38:201-209 (2002).

Sun, M., et al., "Novel Bioactive Phospholipids: Practical Total Syntheses of Products from the Oxidation of Arachidonic and Linoleic Esters of 2-Lysophosphatidylcholine," *J. Org. Chem.*, 67:3575-3584 (2002).

Winkler, B.S., et al., "Oxidative Damage and Age-Related Macular Degeneration," *Molecular Vision*, 5:32 (1999).

Wu, J.T., "Advanced Glycosylation End Products: A New Disease Marker for Diabetes and Aging," *Journal of Clinical Laboratory Analysis*, 7:252-255 (1993).

Jul. 7, 2009, Restriction Requirement, U.S. Appl. No. 12/256,274.

Sep. 8, 2009, Reply to Restriction Requirement, U.S. Appl. No. 12/256,274.

Dec. 9, 2009, Office Action, U.S. Appl. No. 12/256,274.

Jan. 27, 2009, International Preliminary Report on Patentability, PCT/US07/016619.

Jan. 28, 2008, Written Opinion of the International Searching Authority, PCT/US07/016619.

Jan. 28, 2008, International Search Report, PCT/US07/016619.

Nov. 7, 2007, Notification of Transmittal of the International Search Report and the Written Opinion of the International Searching Authority, or the Declaration, PCT/US07/009724.

Nov. 6, 2008, Notification Concerning Transmittal of International Preliminary Report on Patentability, PCT/US07/009724.

Chicheportiche, Y., et al.,"TWEAK, a New Secreted Ligand in the Tumor Necrosis Factor Family That Weakly Induces Apoptosis," *The Journal of Biological Chemistry*, 272(51): 32401-32410 (1997).

Donohue, P.J., et al., "TWEAK Is an Endothelial Cell Growth and Chemotactic Factor That Also Potentiates FGF-2 and VEGF-A Mitogenic Activity," *Arteriorsler Throm Vasc. Biol.*, 23: 594-600 (2003).

Filleur, S., et al., "SiRNA-mediated Inhibition of Vascular Endothelial Growth Factor Severely Limits Tumor Resistance to Antiangiogenic Thrombospondin-1 and Slows Tumor Vascularization and Growth," *Cancer Research*, 63: 3919-3922 (2003).

Lipscomb, E.A., et al., "Use of RNA Interference to Inhibit Integrin ($\alpha 6\beta 4$)-Mediated Invasion and Migration of Breast Carcinoma Cells," *Clinical & Experimental Metastasis*, 20: 569-576 (2003).

Lynch, C.N., et al., "TWEAK Induces Angiogenesis and Proliferation of Endothelial Cells," The *Journal of Biological Chemistry*, 274(13): 8455-8459 (1999).

Martinez. L.A., et al., "Synthetic Small Inhibiting RNAs: Efficient Tools to Inactivate Oncogenic Mutations and Restore p53 Pathways," *PNAS* 99(23): 14849-14854 (2002).

Mignatti, P., et al., "Basic Fibroblast Growth Factor, A Protein Devoid of Secretory Signal Sequence, Is Released by Cells Via a Pathway Independent of the Endoplasmic Reticulum-Golgi Complex," *Journal of Cellular Physiology*, 151: 81-93 (1992).

Nakayama, M., et al., "Fibroblast Growth Factor-Inducible 14 Mediates Multiple Pathways of TWEAK-Induced Cell Death," *The Journal of Immunology*, 170: 341-348 (2003).

Nakayama, M., et al., "Multiple Pathways of TWEAK-Induced Cell Death," *The Journal of Immunology*, 168: 734-743 (2002).

NCBI, (mRNA Sequence) Accession No. AA311507, "EST 182252 Jurkat T-cells V Homo sapiens cDNA5- end,", [retrieved on Apr. 19, 2011] Retreived from the Internet <URL:http://www.ncbi.nlm.gov/nucest/1963845?report=genbank.

NCBI, (mRNA Sequence) Accession No. A1037948, "ox53b11.x1 Soares_total_fetus_Nb2HF8_9w Homo sapiens cDNA clone IMAGE: 1660029 3- Similar to TR:O00581 O00581 Hypothetical 20.5 KD Protein.", [retrieved on Apr. 19, 2011] Retreived from the Internet <URL: http://www.ncbi.nlm.gov/nucest/3277142?report=genbank.

NCBI, (mRNA Sequence) Accession No. AI925946, "wh12f04.x1 NCI_CGAP_Kid11 Homo sapiens cDNA clone Image: 2380543 3- similar to TR:O00581 O00581 Hypothetical 20.5 KD Protein.", [retrieved on Apr. 19, 2011] Retreived from the Internet <URL:http://www.ncbi.nlm.gov/nucest/5661910?report=genbank.

NCBI, (mRNA Sequence) Accession No. AI939311, "qa15d09.x5 NCI_CGAP_Brn23 Homo sapiens cDNA clone Image: 1686833 3- similar to TR:O00581 O00581 Hypothetical 20.5 KD Protein.", [retrieved on Apr. 19, 2011] Retreived from the Internet <URL: http://www.ncbi.nlm.gov/nucest/5678181?report=genbank.

O'Reilly, M.S., "Targeting Multiple Biological Pathyways As A Strategy to Improve The Treatment of Cancer," *Clinical Cancer Research*, 8: 3309-3310 (2002).

Risau, W., "Mechanisms of Angiogenesis," *Nature*, 386: 671-674 (1997).

Saitoh, T., et al., "TWEAK Induces NF-κB2 p100 Processing and Long Lasting NF-κB Activation," *The Journal of Biological Chemistry*, 278(38): 36005-36012 (2003).

Tian, X-L, et al., "Identification of an Angiogenic Factor That When Mutated Causes Susceptibility to Klippel-Trenaunay Syndrome," *Nature*, 427: 640-645 (2004).

Whelan, A. J., et al., "Klippel-Trenaunay-Weber Syndrome Associated With A 5:11 Balanced Translocation," *American Journal of Medical Genetics*, 59: 492-494 (1995).

Wiley, S.R., et al., "A Novel TNF Receptor Family Member Binds TWEAK and Is Implicated in Angiogenesis," *Immunity*, 15: 837-846 (2001).

Wiley, S.R. and Winkles, J.A., "TWEAK, A Member of the TNF Superfamily, Is a Multifunctional Cytokine That Binds The TweakR/Fn14 Receptor," *Cytokine & Growth Factor Reviews*, 14: 241-249 (2003).

Yancopoulos, G.D., et al., "Vascular-Specific Growth Factors and Blood Vessel Formation," *Nature*, 407: 242-248 (2000).

West, X. Z., et al., "Oxidative Stress Induces Angiogenesis by Activating TLR2 With Novel Edogenous Ligands," *Nature*, 467(7318): 972-976 (2010).

Sep. 6, 2010, Office Action, 07836212.6.

Mar. 15, 2011, Reply to Office Action filed, 07836212.6.

* cited by examiner

HSA (0.5 μg)
[7.5 pmol]

CEP-HSA (0.5 μg)
[2.4 pmol]

VEGF (20ng)
[0.7 pmol]

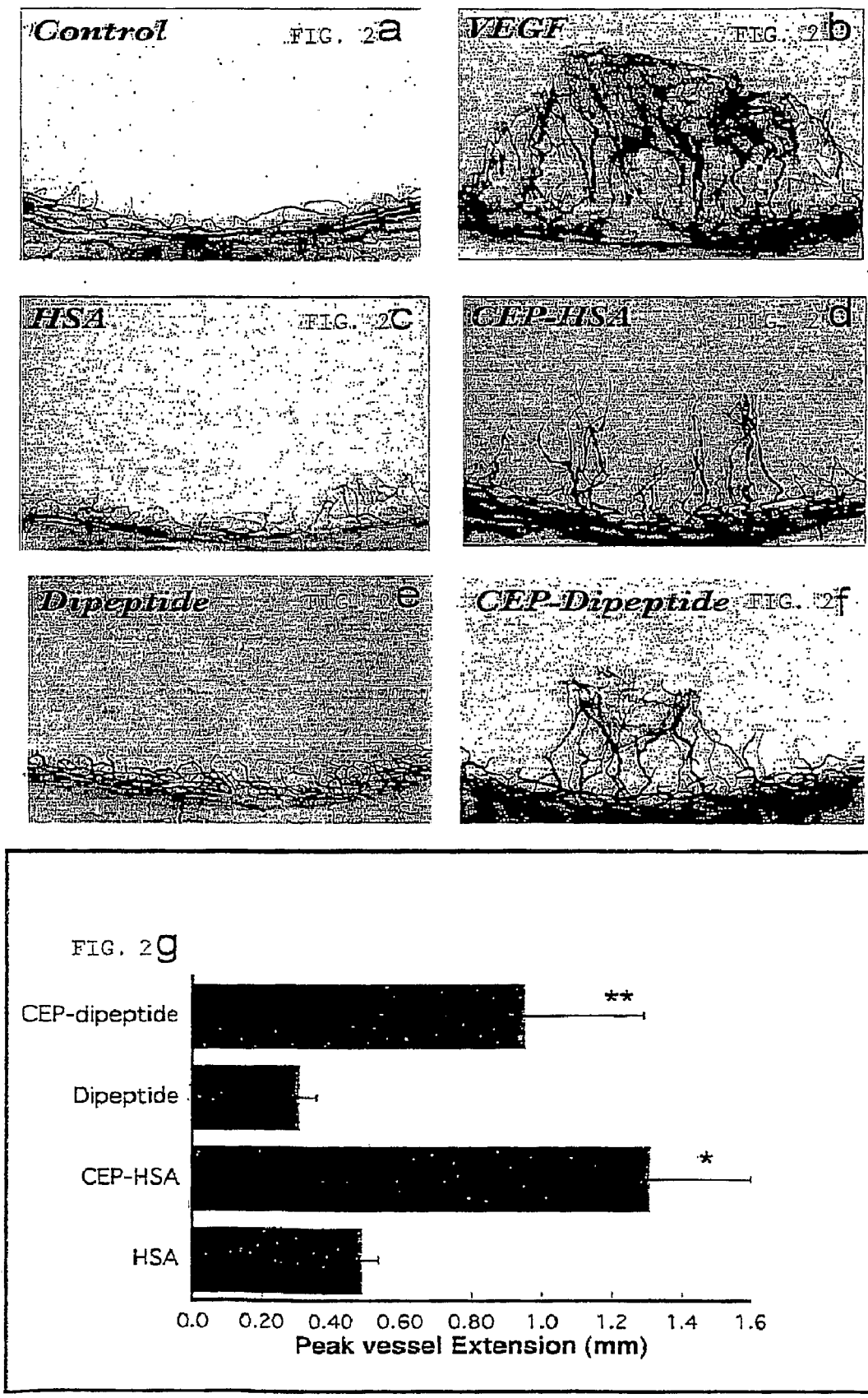

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: CEP Modified Analogue

<400> SEQUENCE: 1

Gly Ser Gly Lys
1

METHODS OF REDUCING ANGIOGENESIS OF AGE-RELATED MACULAR DEGENERATION (AMD) OR CHOROIDAL NEOVASCULARIZATION BY AN ANTI-CARBOXYETHEYLPYRROLE (CFP) ANTIBODY

RELATED APPLICATIONS

This application is the U.S. National Stage of International Application No. PCT/US2007/016619, filed Jul. 23, 2007, published in English, and claims the benefit of U.S. Provisional Application No. 60/832,898, filed on Jul. 24, 2006. The entire teachings of the above application are incorporated herein by reference.

GOVERNMENT SUPPORT

The invention was supported, in whole or in part, by a grant GM 21249 (RGS) from the National Institutes of Health. The Government has certain rights in the invention.

BACKGROUND OF THE INVENTION

Age related macular degeneration (AMD) is the leading cause of blindness in the elderly population in developed countries. Over a third of those over 75 years currently have some form of this disease. Slowing or preventing the progression of AMD is an urgent public health goal. The clinical significance of ocular angiogenesis is enormous, because choroidal neovascularization (CNV) in late stage AMD is the chief cause of irreversible loss of vision in elderly patients in the western hemisphere. CNV involves abnormal vessel growth from the choriocapillaris through Bruch's membrane resulting in hemorrhage, scarring, exudation and/or retinal detachment with the ultimate consequence of severe loss of high acuity central vision. The need for effective therapies to prevent and treat CNV is rapidly growing with the increasing population of people over the age of 65.

SUMMARY OF THE INVENTION

CNV, the advanced stage of AMD affects approximately 10% of patients with AMD, yet accounts for more than 80% of all vision loss in AMD. Carboxyethylpyrrole (CEP) protein modifications, uniquely generated from oxidation of docosahexaenoate-containing lipids are more abundant in ocular tissues from AMD than normal donors and are concentrated in Bruch's membrane, the blood retinal barrier. The investigation of whether CEP protein adducts stimulate angiogenesis and contribute to CNV in AMD is described herein. Human serum albumin (HSA) or dipeptide (acetyl-Gly-Lys-O-methyl ester) were chemically modified to yield CEP-HSA or CEP-dipeptide. The in vivo angiogenic properties of CEP-HSA and CEP dipeptide were evaluated using the chick chorioallantoic membrane and rat corneal micropocket assays. Low picomole amounts of CEP-HSA and CEP dipeptide stimulated neovascularization. Monoclonal anti-CEP antibody neutralized limbal vessel growth stimulated by CEP-HSA while anti-vascular endothelial growth factor (anti-VEGF) antibody only partially neutralized vessel growth. These results show that anti-CEP modalities are useful as therapeutics in treating CNV in AMD.

The studies described herein demonstrate the angiogenic properties of CEP adducts and indicate that CEP plays a role in the development of CNV in late stage AMD. Furthermore, the results show that in vivo blood vessel growth stimulated by CEP can be quantitatively neutralized by anti-CEP antibody but not by anti-VEGF antibody, indicating CEP adducts stimulate angiogenesis in part via a VEGF independent pathway.

Accordingly, the present invention is directed to a method of inhibiting angiogenesis in an individual (e.g., primate such as human) in need thereof, comprising administering to the individual an agent that inhibits one or more carboxyethylpyrrole (CEP) protein adducts, wherein the angiogenesis is the result of oxidative peptide modification of polyunsaturated fatty acids (PUFA), such as docosahexaenoate, in the individual, and administration of the agent inhibits angiogenesis in the individual. The agent can inhibit formation of the CEP protein adducts, activity of the CEP protein adducts (e.g., angiogenic activity) or a combination thereof. The agent can bind to all or a portion of the CEP protein adducts, and includes antibodies or antigen binding fragments thereof having binding specificity for the one or more CEP protein adducts. In a particular embodiment, the antibody is a monoclonal antibody or a single chain FV (scFV) antibody.

The invention is also directed to a method of inhibiting ocular angiogenesis in an individual in need thereof, comprising administering to the individual an agent that inhibits one or more CEP protein adducts wherein administration of the agent inhibits ocular angiogenesis in the individual. In a particular embodiment, the ocular angiogenesis occurs in the retina of the individual.

Also encompassed by the present invention is a method of inhibiting choroidal neovascularization in an individual in need thereof, comprising administering to the individual an agent that inhibits one or more carboxyethylpyrrole (CEP) protein adducts wherein administration of the agent inhibits choroidal neovascularization in the individual. The individual can be at risk for developing age-related macular degeneration or in an early stage of age-related macular degeneration.

The invention is also directed to a method of treating AMD in an individual in need thereof, comprising administering to the individual an agent that inhibits one or more carboxyethylpyrrole (CEP) protein adducts in the individual, thereby treating the AMD. In a particular embodiment, the AMD is at an advanced stage. The AMD can also be characterized by choroidal neovascularization.

BRIEF DESCRIPTION OF THE DRAWINGS

FIGS. 2a-2f are photographs showing that CEP modified HSA as well as dipeptide (Ac-Gly-Lys-OH) induces angiogenesis in a rat corneal micropocket assay. Representative photographs of mouse corneas at 7 days after implantation of pellets containing (FIG. 2a) phosphate buffered saline (PBS) (control), (FIG. 2b) VEGF (100 ng, ~3.5 pmol), (FIG. 2c) HSA (1 µg, ~15 pmol), (FIG. 2d) CEP-HSA (1 µg, ~15 pmol), (FIG. 2e) dipeptide (41 ng, ~112 pmol) or (FIG. 2f) CEP-dipeptide (37 ng, 101 pmol).

FIG. 2g is a bar graph of the results; peak vessel extension was calculated as described in materials and methods. *P<0.005, **p<0.001

DETAILED DESCRIPTION OF THE INVENTION

Figure 1A:
FIGS. 1a-1c are photographs showing that docosahexaenoate lipid-derived oxidatively modified human serum albumin (CEP-HSA) induces angiogenesis in the chorioallantoic membrane (CAM) assay. Chicken CAMs were exposed to pellets containing (FIG. 1a) human serum albumin (HAS) (0.5 µg, ~7.5 pmol), (FIG. 1b) CEP-HSA (0.5 µg, ~7.5 pmol) (FIG. 1c) vascular endothelial growth factor (VEGF) (20 ng, 0.7 pmol) on day 6. Two days later the vessels were injected with India ink and visualized using an Olympus stereomicroscope.

The clinical significance of ocular angiogenesis is enormous, due largely to choroidal neovascularization (CNV) in age-related macular degeneration (AMD) (Group, M. P. S. (1991) *Arch Opthalmol* 109, 1242-57; Group, M. P. S. (1991) *Arch Opthalmol* 109, 1232-41; Campochiaro, P. A. (2000) *J Cell Physiol* 184, 301-10) which is the chief cause of irreversible loss of vision in elderly patients in the western hemisphere. CNV involves abnormal vessel growth from the choriocapillaris through Bruch's membrane resulting in hemorrhage, scarring, exudation and/or retinal detachment with the ultimate consequence of a severe loss of high acuity central vision. The molecular mechanisms involved in the development of CNV are not well defined, but the need for effective therapies to prevent and treat CNV is augmented with an increase in the population of people over the age of 65 years.

CNV, the advanced stage of age-related macular degeneration (AMD) accounts for more than 80% of vision loss in AMD. Carboxyethylpyrrole (CEP) protein modifications, uniquely generated from oxidation of docosahexaenoate-containing lipids are more abundant in Bruch's membrane of AMD retinas. As described herein, whether CEP protein adducts stimulate angiogenesis and contribute to CNV in AMD was investigated. Human serum albumin (HSA) or dipeptide (acetyl-Gly-Lys-O-methyl ester) were chemically modified to yield CEP-HSA or CEP-dipeptide. The in vivo angiogenic properties of CEP-HSA and CEP dipeptide were demonstrated using the chick chorioallantoic membrane and rat corneal micropocket assays. Low picomole amounts of CEP-HSA and CEP dipeptide stimulated neovascularization. Monoclonal anti-CEP antibody neutralized limbal vessel growth stimulated by CEP-HSA while anti-VEGF antibody was found to only partially neutralize vessel growth. In vitro treatments of human retinal pigment epithelial cells with CEP-dipeptide or CEP-HSA did not induce increased VEGF secretion. Overall, these results show that CEP induced angiogenesis utilizes VEGF independent pathways and that anti-CEP therapeutic modalities are likely of value in limiting CNV in AMD.

AMD is a progressive, multifactorial, polygenic disease with poorly understood etiology. Early stages of the disease are typically termed "dry" AMD and associated with the macular accumulation of extracellular deposits (drusen) below the RPE on Bruch's membrane. Geographic atrophy develops in the later stages of dry AMD and is characterized by macular loss of RPE and photoreceptor cells. Advanced stage disease or "wet" AMD is characterized by CNV. Oxidative damage has long been suspected of contributing to AMD (Beatty, S., et al. (2000) *Surv Opthalmol* 45, 115-34; Winkler, B. S. et al. (1999) *Mol Vis* 5, 32), supported by indirect evidence that smoking significantly increases the risk of AMD (Seddon, J. M., et al. (1996) *JAMA* 276, 1141-6) and that antioxidant vitamins and zinc can slow the progression of the disease for select individuals (AREDS (2001) *Arch Opthalmol* 119, 1417-36). Several laboratories have recently shown an association between variants in the complement factor H gene and susceptibility to AMD (Hageman, G. S., et al. (2005) *Proc Natl Acad Sci USA* 102, 7227-32; Klein, R. J., et al. (2005) *Science* 308, 385-9; Edwards, A. O., et al. (2005) *Science* 308, 421-4; Haines, J. L., et al. (2005) *Science* 308, 419-21) implicating inflammatory processes in the pathophysiology of the disease (Bok, D. (2005) *Proc Natl Acad Sci USA* 102, 7053-4). In addition, the recent observation that aged mice exhibiting the apolipoprotein E4 genotype develop a full range of AMD-like pathologies including CNV, when fed a high cholesterol diet suggests that lipid oxidation in combination with genetic and environmental factors might contribute to AMD (Malek, G., et al. (2005) *Proc Natl Acad Sci USA* 102, 11900-5). A previous proteomic study of drusen established a molecular link between oxidative damage and AMD (Crabb, J. W., et al., *Proc. Natl. Acad. Sci. USA*, 99:14682-14887 (2002)) and demonstrated elevated oxidative protein modifications in AMD tissues. Specifically, carboxyethylpyrrole (CEP), a unique protein modification derived from the oxidation of docosahexaenoate (DHA)-containing lipids, was found to be more abundant in AMD compared to normal ocular tissues (Crabb, J. W., et al. (2002) *Proc Natl Acad Sci USA* 99, 14682-7) and was localized in Bruch's membrane between the blood-bearing choriocapillaris and RPE. The outer segments of the photoreceptors contain high concentrations of polyunsaturated fatty acids (PUFAs), especially DHA in the membranes and are exposed to relatively high oxygen tension, close to that found in arterial blood. The photooxidative environment in the retina and the DHA rich photoreceptor outer segments provide a ready source of reactive oxygen species for generating oxidative modifications. PUFAs undergo oxidation in the presence of oxygen or oxygen derived radical species, and elevated levels of CEP-adducts and CEP autoantibodies are present in AMD plasma (Gu, X. et al. (2003) *J. Biol. Chem.*, 273:42027-42035; U.S. Published Application No. 2004/0265924 A1). Described herein is the investigation of whether these oxidative protein modifications are a primary catalyst in drusen formation and play a role in the development of choroidal neovascularization (Crabb, J. W., et al. (2002) *Proc Natl Acad Sci USA* 99, 14682-7). The results of the investigation show that CEP protein modifications induce angiogenesis in vivo.

Levels of CEPs are significantly elevated in patients with AMD versus unaffected individuals. Levels apparently rise strongly in the earliest stage of the disease and then decline, although they remain significantly elevated in all stages of the disease. It is likely that the actual levels of CEPs are not detected because these modified proteins are antigens that induce production of autoantibodies that mask the antigens, especially in the later stages of the disease. It is likely CEP-protein modifications as well as consequent generation of autoantibodies play a role in the etiology of AMD. For example, aggregation of CEP-modified proteins by CEP autoantibodies may contribute to drusen accumulation and promote retinal degeneration. It is likely that CEP levels appear to be highest in the earliest stage of the disease because autoantibodies are not yet present. In later stages of the disease, levels of antigen continue to rise but are not detected because they are present as circulating immune complexes. Plasma from AMD patients exhibited more than a 2-fold higher average CEP autoantibody titer than plasma from age-matched normal controls.

Thus, the present invention pertains to methods of inhibiting angiogenesis in an individual in need thereof comprising administering to the individual an agent that inhibits one or more CEP protein adducts wherein the angiogenesis is the result of oxidative peptide modification of polyunsaturated fatty acids (PUFA) in the individual, and administration of the agent inhibits angiogenesis in the individual. In one embodiment, the invention is directed to methods of inhibiting ocular angiogenesis in an individual in need thereof comprising administering to the individual an agent that inhibits the angiogenic activity of one or more CEP protein adducts wherein administration of the agent inhibits ocular angiogenesis in the individual. In another embodiment, the invention is directed to methods of inhibiting choroidal neovascularization in an individual in need thereof comprising administering to the individual an agent that inhibits the angiogenic activity of one or more CEP protein adducts wherein administration of the agent inhibits choroidal neovascularization in the individual.

The present invention is also directed to methods of treating (prophylactic and/or therapeutic treatment) diseases associated with the angiogenic activity of CEP protein adducts using an agent that inhibits the angiogenic activity of CEP protein adducts. In one embodiment, the invention is directed to a method of treating AMD in an individual in need thereof comprising administering to the individual an agent that inhibits one or more CEP protein adducts.

The terms, "inhibiting" and "treatment" as used herein, refer not only to ameliorating symptoms associated with the condition or disease, but also preventing or delaying the onset of the condition or disease, and/or lessening the severity or frequency of symptoms of the condition or disease. The therapy is designed to inhibit (partially, completely) activity and/or formation of CEP protein adducts in an individual. For example, an agent that inhibits CEP protein adducts can be administered in order to decrease and/or prevent the activity and/or formation of CEP protein adducts.

Figure 6:
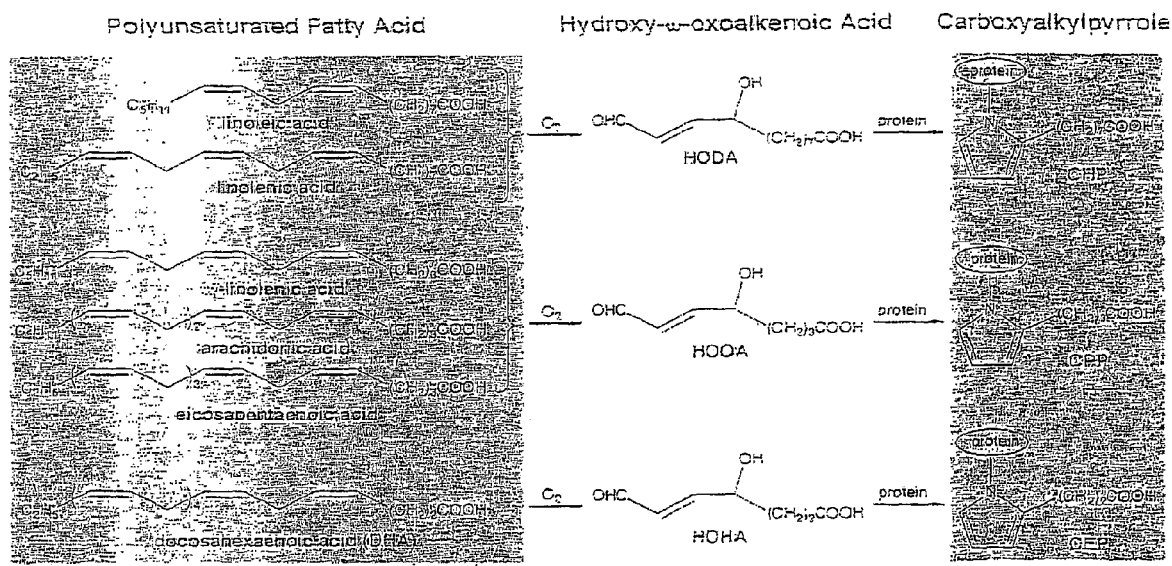
FIG. 6 is an illustrates the generation of 2-(ω-carboxyethyl)pyrrole (CEP) adducts.

Carboxyethylpyrrole (CEP) protein adducts belong to a family of 2-(ω-carboxyalkyl)pyrrole adducts generated from the oxidation of polyunsaturated fatty acids (PUFA) (see Gu et al., *J. Biol. Chem.*, 278(43):42027-42035 (2003) and U.S. Published Application No. 2004/0265924, both of which are incorporated herein by reference). Docosahexaenoic acid (DHA) gives rise to 2-(ω-carboxyethyl)pyrrole adducts, by oxidative cleavage to 4-hydroxy-7-oxohept-5-enoic acid (HOHA) and reaction of the HOHA with protein (FIG. 6). HOHA can form an adduct with a (one or more) primary amine of a peptide (e.g., a dipeptide) or protein resulting in a CEP epitope that is referred to as CEP-peptide or CEP-protein adducts, respectively. For example, HOHA can form an adduct with, or on, proteins such as albumin, and fragments thereof. CEP epitopes can also be generated by the reaction of HOHA with the primary amino group of ethanolamine phospholipids that are referred to as ethanolamine phospholipid CEP adducts. Also phospholipids containing an HOHA residue can form CEPs through reaction with primary amino groups of biomolecules such as proteins followed by phospholipolysis of the initially formed CEP phospholipid ester derivative.

An agent that inhibits a (one or more) CEP protein adduct is an agent or compound that inhibits the activity and/or formation (expression) of a CEP protein adduct, as described herein (e.g., a CEP protein adduct antagonist). An agent that inhibits a CEP protein adduct can alter CEP protein adduct activity or CEP protein adduct formation by a variety of means. The inhibition can be partial or complete inhibition of CEP protein adduct activity and/or formation. In addition, the agent can inhibit the CEP protein adduct directly (specifically interact) or indirectly (non-specifically interact).

For example, the agent for use in the methods of the present invention can inhibit one or more biological activities of CEP protein adducts. An example of a biological activity of a CEP protein adduct is angiogenic activity. In one embodiment, the agent binds to all or a portion (e.g., a portion of the CEP protein adduct; the CEP portion of the CEP protein adduct; the protein or peptide portion of the CEP protein adduct) of the CEP protein adduct under conditions in which the angiogenic activity of the CEP protein adduct is inhibited.

Alternatively, the agent for use in the methods of the present invention can inhibit formation of the CEP protein adduct. For example, the agent can prevent CEP protein adducts from forming, and/or hydrolyze CEP protein adducts that have previously formed, regenerating the primary amino group found in the unmodified biomolecule. In one embodiment, the agent can interact with HOHA or its esters, e.g., phospholipid derivatives containing a HOHA acyl group esterified to the sn-2 position, and/or the protein which forms an adduct with HOHA, prior to formation of the CEP protein adduct, thereby preventing CEP protein adducts from forming. In addition, the agent can interact with an upstream product (e.g., DHA) of the reaction which leads to formation of CEP protein adducts in order to prevent CEP protein adducts from forming.

The agent can also interact with the CEP protein adduct or portion thereof after CEP protein adducts have formed, for example, under conditions in which the pyrrole moiety of the CEP and the protein of the CEP protein adduct is disrupted. In particular embodiments, the agent cleaves the CEP group from the protein.

Examples of agents which can inhibit receptor-mediated effects of CEP protein adducts include the following: nucleic acids, fragments or derivatives thereof and vectors comprising such nucleic acids (e.g., a nucleic acid molecule, cDNA, and/or RNA); polypeptides; peptidomimetics; fusion proteins or prodrugs thereof; antibodies; ribozymes; aptamers; small molecules; and other compounds that inhibit CEP protein adduct activity and/or formation. One or more agents that inhibit CEP protein adducts can be used concurrently (simultaneously) or sequentially in the methods of the present invention, if desired.

In a particular embodiment, the agent or compound that inhibits CEP protein adduct activity and/or formation is an antibody (e.g., a polyclonal antibody; a monoclonal antibody). For example, antibodies that bind all or a portion of one or more CEP protein adducts and that inhibit CEP protein adduct activity can be used in the methods described herein (Gu et al., *J. Biol. Chem.*, 278(43):42027-42035 (2003) and U.S. Application No. 2004/0265924, both of which are incorporated herein by reference). In a particular embodiment, the antibody is a purified antibody. The term "purified antibody" as used herein refers to immunoglobulin molecules and immunologically active portions of immunoglobulin molecules, i.e., molecules that contain an antigen binding site that selectively binds all or a portion (e.g., a biologically active portion) of a CEP protein adduct. A molecule that selectively binds to a CEP protein adduct is a molecule that binds to a CEP protein adduct or a fragment thereof, but does not substantially bind other molecules in a sample (e.g., a biological sample that naturally contains the CEP protein adduct). Preferably the antibody is at least 60%, by weight, free from proteins and naturally occurring organic molecules with which it naturally associated. More preferably, the antibody preparation is at least 75% or 90%, and most preferably, 99%, by weight, antibody. Examples of immunologically active portions of immunoglobulin molecules include F(ab) and F(ab')$_2$ fragments that can be generated by treating the antibody with enzymes such as pepsin or papsain, and single chain FV (scFV) fragments.

The term "monoclonal antibody" or "monoclonal antibody composition," as used herein, refers to a population of antibody molecules that contain only one species of an antigen binding site capable of immunoreacting with a particular epitope of a CEP protein adduct of the invention. A monoclonal antibody composition thus typically displays a single binding affinity for a particular CEP protein adduct of the invention with which it immunoreacts.

Polyclonal antibodies can be prepared using known techniques such as by immunizing a suitable subject with a desired immunogen, e.g., a CEP protein adduct or fragment thereof. The antibody titer in the immunized subject can be monitored over time by standard techniques, such as with an enzyme linked immunosorbent assay (ELISA) using immobilized polypeptide. If desired, the antibody molecules directed against the CEP protein adduct can be isolated from the mammal (e.g., from tissue, blood) and further purified by well-known techniques, such as protein A chromatography to obtain the IgG fraction.

At an appropriate time after immunization (e.g., when the antibody titers are highest) antibody-producing cells can be obtained from the subject and used to prepare monoclonal antibodies by standard techniques, such as the hybridoma technique originally described by Kohler and Milstein, Nature 256:495-497 (1975), the human B cell hybridoma technique (Kozbor et al., Immunol. Today 4:72 (1983)), the EBV-hybridoma technique (Cole et al., Monoclonal Antibodies and Cancer Therapy, Alan R. Liss, Inc., pp. 77-96 (1985)) or trioma techniques. The technology for producing hybridomas is well known (see generally Current Protocols in Immunology, Coligan et al., (eds.) John Wiley & Sons, Inc., New York, N.Y. (1994)). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a CEP protein adduct of the invention.

Any of the many well known protocols used for fusing lymphocytes and immortalized cell lines can be applied for the purpose of generating a monoclonal antibody to a CEP protein adduct of the invention (see, e.g., Current Protocols in Immunology, supra; Galfre et al., Nature, 266:55052 (1977); R. H. Kenneth, in Monoclonal Antibodies: A New Dimension In Biological Analyses, Plenum Publishing Corp., New York, N.Y. (1980); and Lerner, Yale J. Biol. Med. 54:387-402 (1981)). Moreover, the ordinarily skilled worker will appreciate that there are many variations of such methods that also would be useful.

In one alternative to preparing monoclonal antibody-secreting hybridomas, a monoclonal antibody to a CEP protein adduct of the invention can be identified and isolated by screening a recombinant combinatorial immunoglobulin library (e.g., an antibody phage display library) with the CEP protein adduct to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Hum. Antibod. Hybridomas 3:81-85 (1992); Huse et al., Science 246:1275-1281 (1989); and Griffiths et al., EMBO J. 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In a particular embodiment, the antibody is a scFV antibody which binds CEP protein adducts. One of skill in the art can obtain an scFV phage displayed combinatorial antibody library that can be used to generate scFV antibodies which bind CEPs. Selection of phages displaying scFV which bind CEPs can be accomplished using, for example, CEP derivatives of biotinylated peptides anchored to streptavidin-coated magnetic beads, a technology that facilitates extensive washing that reduces non-specific interactions of the phage (Sawyer, C., et al., *J. Immunol. Methods,* 204: 193-203 (1997)). To "pan" for scFV-CEP antibodies the efficacy of a CEP derivative, such as btn-NH(CH$_2$)$_6$-CEP prepared by a general synthesis of biotinylated haptens can be determined. If necessary, a biotinylated analogue, btn-GLyLys-CEP, of Ac-GLyLys) OMe)-CEP (a biologically active "CEP-dipeptide"), can be prepared. In addition, a longer flexible linker using a CEP-modified analogue of the btn-GlySerGlyLys-isoLGE$_2$-lactam (SEQ ID NO:1) can be used.

The antibodies for use in the methods of the present invention can also be capable of detection, for example, in order to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, and acetylcholinesterase; examples of suitable prosthetic group complexes include streptavidin/biotin and avidin/biotin;

examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferase, luciferin, green fluorescent protein, and acquorin, and examples of suitable radioactive material include, for example, $^{125}I$, $^{131}I$, $^{35}S$, $^{32}P$ and $^{3}H$.

The agents which inhibit CEP protein adducts are administered in a therapeutically effective amount (i.e., an amount that is sufficient to treat or inhibit the disease or condition, such as by ameliorating symptoms associated with the disease or condition, preventing or delaying the onset of the disease or condition, and/or also lessening the severity or frequency of symptoms of the disease or condition). The amount that will be therapeutically effective in the treatment of a particular individual's disorder or condition will depend on the symptoms and severity of the disease, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The methods of the present invention can be used to treat any suitable individual. In one embodiment, the individual is a primate. In a particular embodiment, the individual is a human.

The agent (e.g., therapeutic compound) can be delivered in a composition, as described above, or by themselves. They can be administered systemically, or can be targeted to a particular tissue. The therapeutic compounds can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein. A combination of any of the above methods of treatment can also be used.

The compounds for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy, rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In another embodiment, the invention is directed to agents which inhibit CEP protein adducts for use as a medicament in therapy. For example, the agents identified herein can be used in the treatment of optic nerve damage. In addition, the agents identified herein can be used in the manufacture of a medicament for the treatment of AMD.

Use of the agents described herein to inhibit or treat diseases or conditions associated with CEP protein adducts can be used in conjunction with other known therapies for such diseases or conditions. For example, anti-VEGF therapies with recombinant humanized anti VEGF monoclonal antibody or aptamer are being evaluated as treatments for CNV. However, the ability of VEGF neutralizing antibody to only partially block CEP-HSA induced angiogenesis indicates that additional therapeutics will be required to effectively limit CNV. CEP neutralization modalities can be effective independently or as a complement to anti-VEGF therapies for the inhibition of CNV in AMD.

EXEMPLIFICATION

Methods

Synthesis of ω-Carboxyethylpyrrole-Modified Proteins and Peptides

Unambiguous production of 2-(ω-carboxyethyl)pyrrole (CEP) was established utilizing the γ-ketoaldehydes, 4,7-dioxoheptanoic acid (DOHA) as described previously (Gu, X., et al. (2003) *J Org Chem* 68, 3749-3761). Paal-Knorr condensation of DOHA with human serum albumin (HSA) and with the dipeptide acetyl-Gly-Lys-O-methyl ester were used to generate CEP-HSA and CEP-dipeptide, respectively, which were characterized by mass spectrometry and NMR as described previously (Gu, X., et al. (2003) *J Org Chem* 68, 3749-3761). Pyrrole concentration was determined by Ehlrich's assay with 4-(dimethylamino)benzaldehyde and absorbance at 570 nm. Protein was quantified by amino acid analysis (Crabb, J. W., et al. (1997) Amino Acid Analysis (John Wiley and Sons, Inc.)) and the Bradford protein assay.

Chick Chorio Allantoic Membrane (CAM) Angiogenesis Assay

The CAM assay was performed as described previously (Nguyen, M., et al. (1994) *Microvasc Res* 47, 31-40) with slight modifications. Fertilized 3-day old white Leghorn eggs (CWRU, Squire valley farms) were cracked, and embryos with the yolk intact were placed in 100 mm×20 mm glass bottom Petri dishes. Following incubation for 3 days at 37° C. in 3% $CO_2$, a methylcellulose disc (Fisher Scientific, Fair Lawn, N.J.) containing CEP-HSA or CEP-dipeptide, was placed on the CAM of individual embryos. CAMs implanted with discs loaded with unmodified dipeptide, HSA, control buffer or with vascular endothelial growth factor (VEGF) were used as negative and positive controls respectively. After 48 hours of incubation, India ink was injected into the vascular system for better visualization of the vessels by a stereomicroscope. Images were captured with a Panasonic CCD camera. Samples were always compared on the same CAM to avoid egg-to-egg variability. For quantitative analysis of vessel density and leakage, CAM images were batch processed using customized macros generated in Image-Pro Plus 5.0 (Media Cybernetics, Silver Spring, Md.). Briefly, a region of interest (ROI) was traced around grafted tissue in each image, each image was then cropped to its ROI, converted to grayscale, and processed using a large spectral filter to enhance the appearance of vasculature whilst omitting presence of larger vessels (determined by filter width). For skeletal density and vessel leakage measurements images were skeletonized using morphological filters (pixels representing branch points were excluded to divide vasculature into distinct vessel segments). Lengths of skeletal segments larger than 5 pixels (delineating vessels) were summed and divided by total graft area for skeletal density. Conversely, skeletal segments smaller than 5 pixels were summed for vessel leakage measurement.

Rat Corneal Micropocket Assay

Hydron/sucralfate pellets containing unmodified or CEP modified HSA or dipeptide with or without neutralizing antibodies (monoclonal mouse anti-human VEGF, 1.5 μg, R&D systems (MAB293) or monoclonal anti-CEP antibody (Gu, X., et al. (2003) *J. Biol. Chem.*), 4 μg) were inserted into corneal micropockets (1 mm from the limbus) of Sprague-Dawley rats. Control mouse IgM, 4 μg (eBioscience, cat. #14-4752) and mouse IgG, 1.5 μg (Southern Biotechnology Inc., cat. #0104-01) antibodies were used in control pellets for comparison with anti-CEP and anti-VEGF antibodies respectively. Corneas were examined daily with the aid of a surgical microscope to monitor angiogenic responses to CEP modified peptide or proteins. To photograph the angiogenic response, animals were perfused with India ink to label the vessels, and following enucleation and fixation, the corneas were excised, flattened and photographed. A positive neovascularization response was recorded only if sustained directional in-growth of capillary sprouts and hairpin loops toward the pellet was observed. A negative response was recorded when either no growth is observed or only an occasional sprout or hairpin loop showing no evidence of sustained growth was detected. All responses were compared to a negative control (pellet and pellet containing buffer) and positive control of VEGF. For neutralization studies, responses were compared to a negative control of non-specific mouse immunoglobulin (IgM) described above. Angiogenic response was analyzed for peak vascular extension and total skeletal (vascular) length using Image-Pro Plus 5.0 (Media Cybernetics, Silver Spring, Md.). Prior to performing vessel measurements images were processed using best-fit equalization filters, spectral filters, and large pixel-width background removal filters to enhance vasculature and eliminate image artifacts. For total skeletal length measurements, processed images were skeletonized, summing pixel lengths of resultant skeletal segments. To determine peak vessel extension, processed images were thresholded for vasculature, filling in holes between adjacent vessels using morphological filters. The resulting image, a single segmented object representing the overall dimensions of the vascular bed, was analyzed for maximum box-width, i.e. extent of vessel penetration.

Cell Culture Conditions and VEGF Secretion Assay.

Human retinal pigment epithelium (ARPE-19) cells were cultured in DMEM/F-12 medium with 10% fetal bovine serum, 100 U/ml penicillin, and 100 μg/ml streptomycin. The medium was changed every four days and all studies were performed on confluent cells. Endotoxin free media and serum were used. Confluent cultures in 24 well plates were starved for three days with serum free medium before incubating with CEP-Dipeptide or CEP-HSA (0.1-0.10 μM) and unmodified dipeptide or HSA (as controls). The CEP-dipeptide, CEP-HSA and controls were quantified by amino acid analysis (Crabb, J. W., et al. (1997) Amino Acid Analysis (John Wiley and Sons, Inc.)). Supernatant media was collected to measure VEGF secretion using an enzyme-linked immunosorbent assay (ELISA) according to the manufacturer's protocol (Research Diagnostics, Flanders, N.J.). Concanavalin (50 μg/mL) was used as a positive control for VEGF stimulation.

Statistical Analysis Data are Presented as Mean±SD.

The statistical significance of differential findings observed between experimental and control groups was determined using one-way analysis of variance (ANOVA), and considered to be significant if P values were <0.06.

Results

CEP-Induced Angiogenesis in Chicken Embryo.

Figure 1B:
Figure 1C:
Figure 1D:
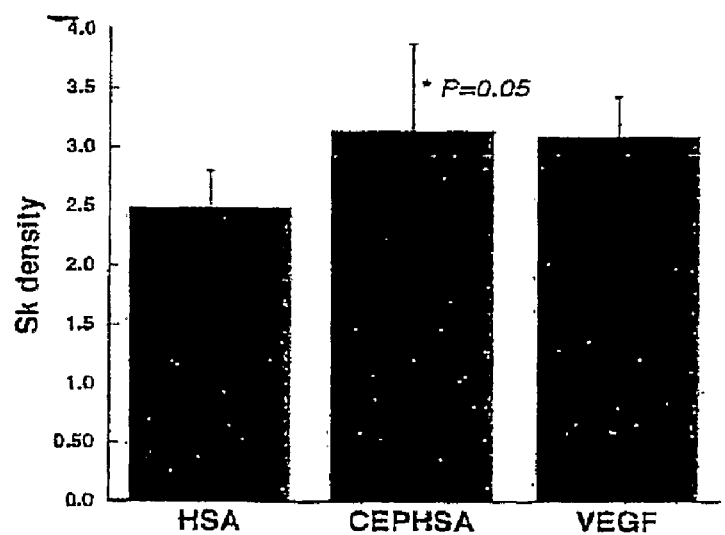
FIG. 1d is a bar graph of the results.

The potential consequence of CEP modified human serum albumin (CEP-HSA) on angiogenesis was examined using the chick chorioallantoic membrane (CAM) assay. The angiogenic response to methylcellulose discs containing 0.5 μg (n=4), 1 μg (n=3), and 10 μg (n=4) of CEP-HSA or unmodified HSA (n=8) was analyzed. The protein preparations were analyzed for endotoxin and determined to be free of contamination. Representative results from these CAM assays are depicted in FIGS. 1a-1d. CEP-HSA (FIG. 1b)

induced sprouting of new blood vessels that appeared to be tortuous and leaky when perfused with India ink. The average skeletal density of CAM vessels with 0.5 µg of CEP-HSA was ~3.1. Unmodified HSA (0.5 µg) did not show this effect (FIG. 1a) with quantitation revealing a lower background skeletal density of ~2.5. Vascular endothelial growth factor (VEGF 20 ng) was used as a positive control (FIG. 1c) and showed an average skeletal density of ~3.1 in the CAM assay. CEP-HSA (161 ng) induced a maximal response compared with minimal or absent response with HSA at doses up to 0.5 µg. The angiogenic response of 161 ng CEP-HSA (2.4 pmol) was similar to the half maximal response of VEGF at a dose of 20 ng (0.7 pmol).

CEP-Induced Angiogenesis in Rat Cornea.

The results from the CAM assay were confirmed and extended in rats using an additional in vivo angiogenesis assay, the corneal micropocket assay. Pellets containing CEP-HSA, (1 µg, FIG. 2d) or CEP modified dipeptide (CEP-dipeptide, 37 ng, FIG. 2f) when implanted 1 mm from the limbus of rat cornea stimulated the growth of limbal blood vessels towards the pellet. The newly formed capillaries reached the pellet by day 7 in all the animals implanted with 1 µg or more of CEP-HSA (n=5), or 37 ng or more of CEP-dipeptide (n=7). Notably, unmodified HSA (1 µg n=3, FIG. 2c) or dipeptide (41 ng, n=6, FIG. 2e) did not induce this effect. Discs containing no protein or peptide were used as a negative control (FIG. 2a) and VEGF discs (100 ng, FIG. 2b) generated the positive control. A statistically significant increase in peak vessel extensions were observed in response to CEP-HSA (~23 fold) or CEP-dipeptide (~3.1 fold) when compared with unmodified parent molecules (FIG. 2g).

Neutralization of CEP Induced Angiogenesis with Anti-CEP but not Anti-VEGF Antibodies.

Figure 3A:
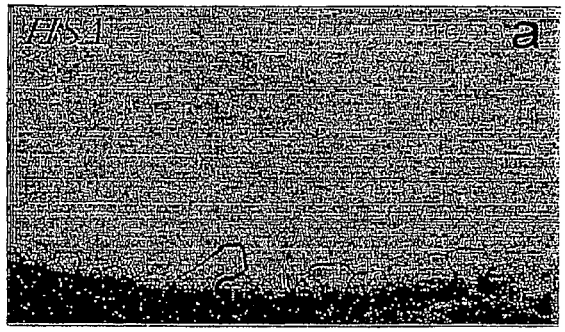
FIGS. 3a-3d are photographs showing neutralization of CEP-HSA induced angiogenesis by monoclonal anti-CEP antibody. Representative photographs of mouse corneas at 7 days following implantation of pellets containing (FIG. 3a) HSA (10 μg, ~149 pmol), (FIG. 3b) CEP-HSA (1 μg, ~15 pmol), (FIG. 3c) CEP-HSA (1 μg) with non specific mouse IgM control antibody and (FIG. 3d) CEP-has (1 μg) with monoclonal anti CEP antibody.
Figure 3B:
Figure 3C:
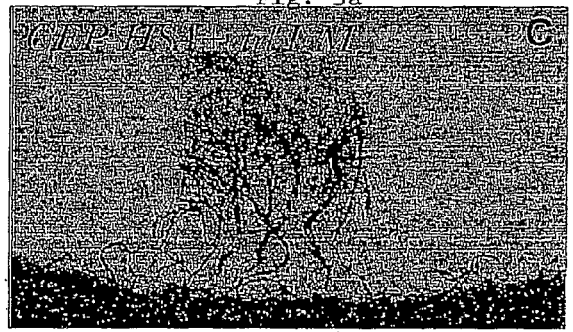
Figure 3D:
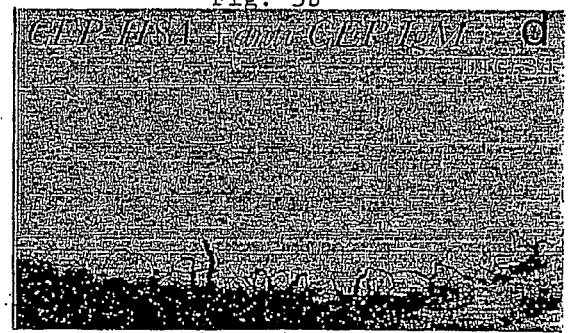
Figure 3E:
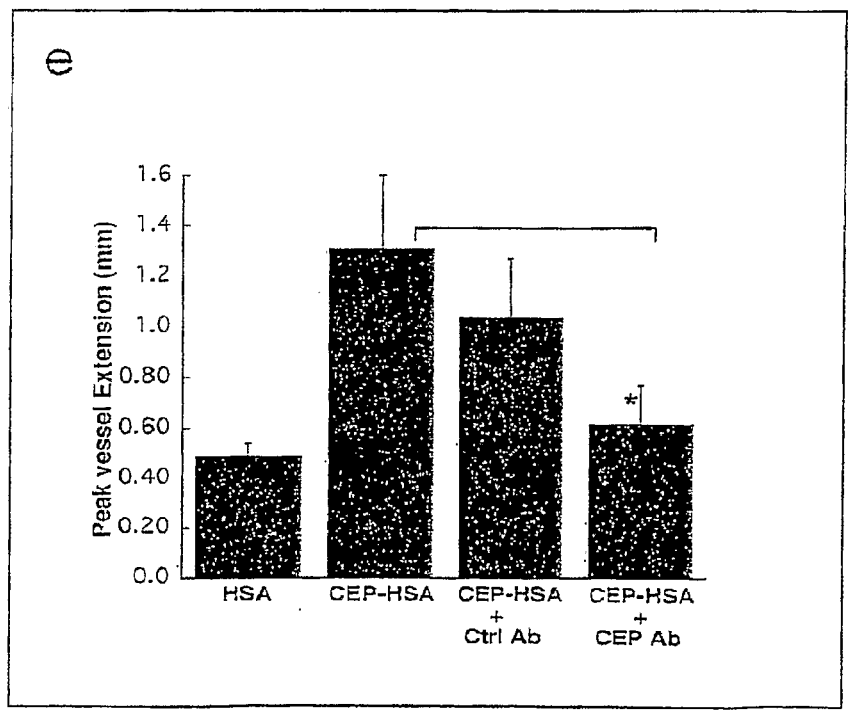
FIG. 3e is a bar graph of the results; peak vessel extension was calculated as described in material and methods. *P<0.05
Figure 4A:
FIGS. 4a-4d are photographs showing incomplete neutralization of CEP-HSA induced angiogenesis by monoclonal anti-VEGF antibody. Representative photographs of mouse corneas at 7 days following implantation of pellets containing (FIG. 4a) CEP-HSA (1 μg, ~15 pmol), (FIG. 4b) CEP-HSA (1 μg) with anti-VEGF neutralizing antibody (FIG. 4c) VEGF (20 ng, ~0.7 pmol) and (FIG. 4d) VEGF (20 ng) with anti-VEGF neutralizing antibody.
Figure 4C:
Figure 4B:
Figure 4D:
Figure 4E:
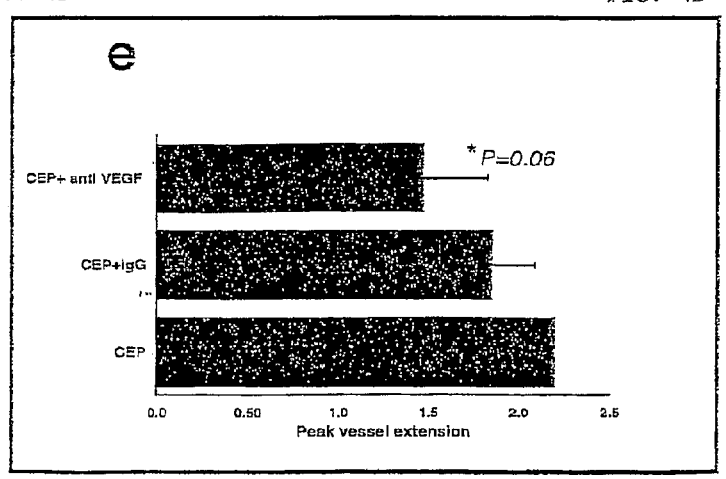
FIG. 4e is a bar graph of the results; peak vessel extension was calculated as described in material and methods. *P=0.06, CEP-HSA+control IgG versus CEP-HSA+anti-VEGF.

To confirm that the angiogenesis was induced by CEP modification of HSA, pellets were prepared by premixing anti-CEP antibody (see U.S. Published Application No. 2004/0265924) or anti-VEGF antibody (R&D Systems, cat. #MAB293) and CEP-HSA. The monoclonal anti-CEP antibody almost completely inhibited the formation of new blood vessels from CEP-HSA implants (FIG. 3d) in the corneal micropocket assay. Neutralizing VEGF antibody only partially inhibited the CEP-HSA induced neovascularization response (FIGS. 4a, 4b, 4e) while completely inhibiting VEGF induced response (FIGS. 4c, 4d). Control mouse IgM or IgG antibodies did not show inhibition of CEP-HSA mediated corneal neovascularization (FIGS. 3c, 4e). Quantitation of peak vessel extensions indicates that the observed neutralization of CEP-HSA induced angiogenesis by anti-CEP was of greater statistical significance than by anti-VEGF antibodies (FIGS. 3e, 4e).

CEP Adducts do not Stimulate VEGF Secretion In Vitro.

Figure 5:
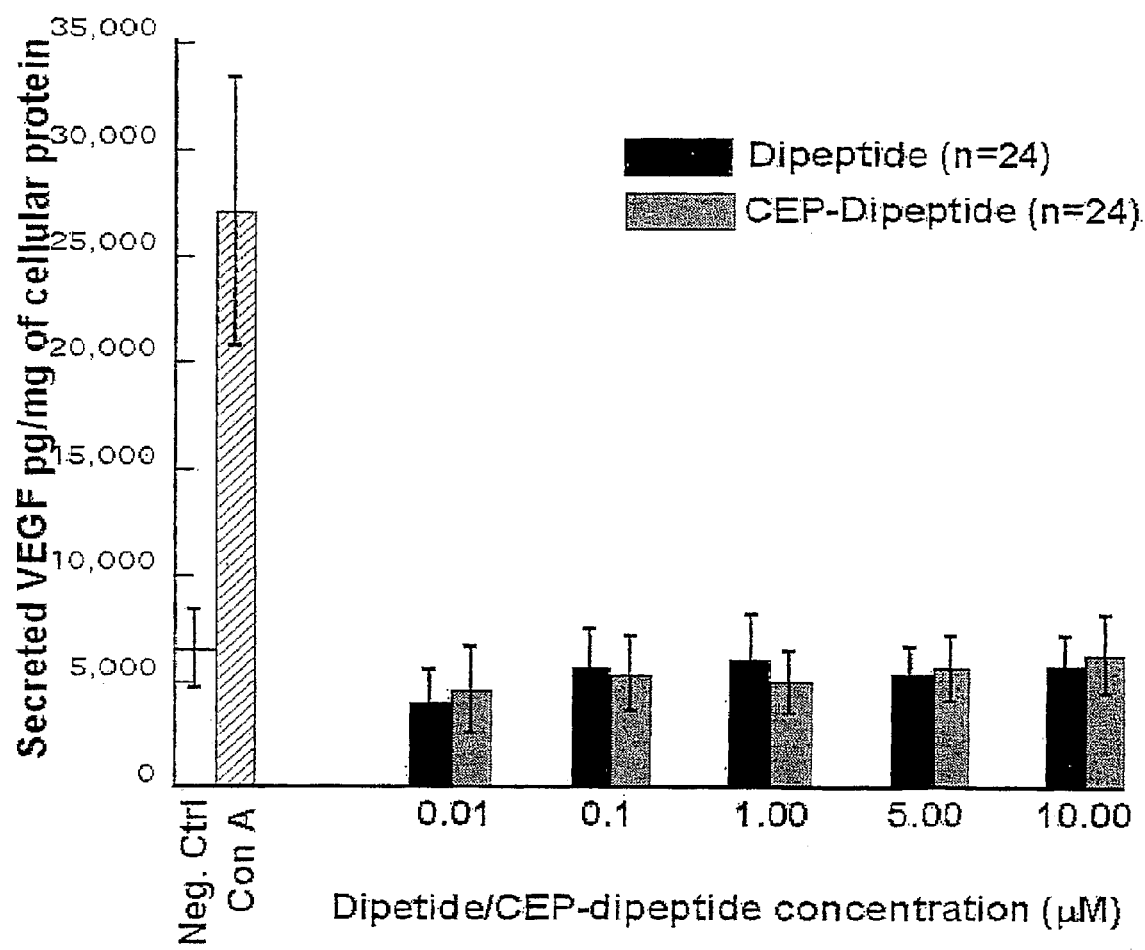
FIG. 5 is a bar graph showing that CEP dipeptide does not increase secretion of VEGF in RPE cells. Human ARPE-19 cells were exposed to various concentrations of dipeptide or CEP-dipeptide. VEGF concentrations were measured in the conditioned medium of cells after 18 hours. VEGF is expressed in pg/mg of cellular protein. All data are from n=4 independent experiments in which each condition was assayed 6× per experiment; error bars represent standard deviation.

Another type of oxidized protein modification, namely advanced glycation end products (AGEs), stimulate angiogenesis in vivo (Okamoto, T., et al. (2002) Microvasc Res 63, 186-95) and induce VEGF secretion in vitro (Hirata, C., et al. (1997) Biochem Biophys Res Commun 236, 712-5; Hoffmann, S., et al. (2000) Invest Opthalmol Vis Sci 41, 2389-93). To explore whether CEP adducts influence VEGF secretion in vitro, human retinal pigment epithelial (RPE) cells were treated with CEP-dipeptide (0.1-10 µM) and VEGF protein quantified in the growth media by ELISA. CEP-dipeptide treated ARPE19 cells did not exhibit increased VEGF in the growth media relative to the unmodified dipeptide or media alone (FIG. 5). ARPE19 cells treated with CEP-HSA (0.1-10 µM) also exhibited no increase in VEGF secretion (data not shown).

Discussion

CEP protein adducts belong to a family of 2-(ω-carboxyalkyl)pyrrole adducts generated from the oxidation of polyunsaturated fatty acids (PUFAs) (Kaur, K., et al. (1997) Chem Res Toxicol 10, 1387-96). For example, oxidative fragmentation of linoleic acid or arachidonic acid can generate 2-(ω-carboxyheptyl)pyrrole (CHP) or 2-(ω-carboxypropyl)pyrrole (CPP) adducts, respectively. The phosphatidylcholine (PC) esters of the oxidatively truncated PUFA progenitors of these adducts are biologically active and present in atherosclerotic plaques (Podrez, E. A., et al. (2002) J Biol Chem 277, 38517-23; Podrez, E: A., et al. (2002) J Biol Chem 277, 38503-16; Subbanagounder, G., et al. (2002) Vascul Pharmacol 38, 201-9; Sun, M., et al. (2002) J Org Chem 67, 3575-84). However, while CPP or CHP protein adducts can also arise from oxidation of other common PUFAs, CEP protein adducts uniquely are generated from oxidation of DHA (Gu, X., et al. (2003) J Org Chem 68, 3749-3761). Although rare in most human tissues, DHA accounts for approximately 80 mol % of the polyunsaturated lipids in photoreceptor outer segments (Fliesler, S. J. & Anderson, R. E. (1983) Prog Lipid Res 22, 79-131). The abundance of DHA in photoreceptors, the high photooxidative stress in the retina as well as the fact that DHA is the most oxidizable fatty acid in humans, all contribute to the higher levels of CEP-adducts in AMD. Interestingly, CEP immunoreactivity and CEP autoantibody titer are also significantly elevated in plasma from AMD donors (Gu, X., et al. (2003) J. Biol. Chem.), and are likely of diagnostic utility as biomarkers for predicting AMD susceptibility. Other oxidative modifications such as advanced glycation end products (AGEs), generated from oxidized carbohydrate products also accumulate during aging (Handa, J. T., et al. (1999) Invest Opthalmol Vis Sci 40, 775-9; Wu, J. T. (1993) J Clin Lab Anal 7, 252-5), especially in the choriocapillaris, Bruch's membrane (Handa, J. T., et al. (1999) Invest Opthalmol Vis Sci 40, 775-9) and CNV membranes (Ishibashi, T., et al. (1998) Arch Opthalmol 116, 1629-32). Several studies have shown that AGEs can stimulate the proliferation of choroid endothelial cells, the expression of MMP-2 and growth factors such as VEGF (Hoffmann, S., et al. (2002) Graefes Arch Clin Exp Opthalmol 240, 996-1002) and angiogenesis in vivo (Okamoto, T., et al. (2002) Microvasc Res 63, 186-95).

The present study demonstrates the angiogenic properties of CEP adducts and suggests the possibility of CEP playing a role in the development of the wet (exudative) form of AMD. However, the molecular mechanism by which CEP induces angiogenesis has not yet been determined. A likely indirect mechanism for in vivo CEP stimulation of angiogenesis is that CEP induces the release of angiogenic factors such as VEGF or basic fibroblast growth factor (bFGF) by epithelial cells, or inhibits the secretion of angiogenesis inhibitors that might contribute to the induction of angiogenesis. The ability of VEGF neutralizing antibody to only partially block CEP-HSA induced angiogenesis in vivo and the lack of increase in VEGF secretion in RPE cells exposed to CEP-modified dipeptide or CEP-HSA, indicates the utilization of additional VEGF independent pathways.

All publications and patent documents cited in this disclosure are incorporated by reference in their entirety. The citation of any references herein is not an admission that such references are prior art to the present invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of reducing angiogenesis in an individual in need thereof, comprising administering to the individual an anti-carboxyethylpyrrole (CEP) antibody, wherein the angiogenesis is the result of oxidative peptide modification of polyunsaturated fatty acids (PUFA) in the individual, and administration of the antibody reduces angiogenesis in the individual.

2. The method of claim 1 wherein the PUFA is docosahexaenoate.

3. The method of claim 1 wherein the antibody inhibits formation of the CEP protein adducts, activity of the CEP protein adducts or a combination thereof.

4. The method of claim 3 wherein the antibody binds to all or a portion of the CEP protein adducts.

5. The method of claim 1 wherein the one or more CEP protein adducts is a CEP-albumin adduct.

6. The method of claim 1 wherein the angiogenesis is ocular angiogenesis.

7. A method of reducing choroidal neovascularization (CNV) in an individual in need thereof wherein the CNV is the result of oxidative peptide modification of polyunsaturated fatty acids (PUFA) in the individual, comprising administering to the individual an anti-carboxyethylpyrrole (CEP) antibody wherein administration of the antibody reduces the CNV in the individual.

8. The method of claim 7 wherein the individual is at risk for developing age-related macular degeneration or in an early stage of age-related macular degeneration.

9. The method of claim 7 wherein the antibody inhibits formation of the CEP protein adducts, activity of the CEP protein adducts or a combination thereof.

10. The method of claim 7 wherein the antibody binds to all or a portion of the CEP protein adducts.

11. The method of claim 7 wherein the one or more CEP protein adducts is a CEP-albumin adduct.

12. The method of claim 7 wherein the ocular angiogenesis occurs in the retina of the individual.

13. A method of reducing angiogenesis of age-related macular degeneration (AMD) in an individual in need thereof wherein the angiogenesis is the result of oxidative peptide modification of polyunsaturated fatty acids (PUFA) in the individual, comprising administering to the individual an anti-carboxyethylpyrrole (CEP) antibody, thereby reducing the angiogenesis of the AMD.

14. The method of claim 13 wherein the AMD is at an advanced stage.

15. The method of claim 13 wherein the antibody inhibits formation of the CEP protein adducts, activity of the CEP protein adducts or a combination thereof.

16. The method of claim 13 wherein the antibody binds to all or a portion of the CEP protein adducts.

17. The method of claim 13 wherein the one or more CEP protein adducts is a CEP-albumin adduct.

* * * * *

UNITED STATES PATENT AND TRADEMARK OFFICE
CERTIFICATE OF CORRECTION

PATENT NO. : 8,137,991 B2  
APPLICATION NO. : 12/374747  
DATED : March 20, 2012  
INVENTOR(S) : John W. Crabb et al.

Page 1 of 1

It is certified that error appears in the above-identified patent and that said Letters Patent is hereby corrected as shown below:

On the Title Page of the patent in the Title field (54) delete "(CFP)" and insert --(CEP)--.

On the Title page of the patent in the PCT No. field (86) under §371(c)(l), (2), (4) Date delete "January 22, 2009" and insert --April 29, 2009--.

In Column 1, Line 5 delete "(CFP)" and insert --(CEP)--.

Signed and Sealed this  
Tenth Day of July, 2012

David J. Kappos  
*Director of the United States Patent and Trademark Office*